United States Patent [19]

Coller et al.

[11] Patent Number: 5,455,228

[45] Date of Patent: Oct. 3, 1995

[54] PEPTIDASE RESISTANT THROMBIN RECEPTOR PEPTIDE LIGAND

[75] Inventors: Barry S. Coller, Dix Hills; Glenn D. Prestwich, Head-of-the-Harbor, both of N.Y.

[73] Assignee: The Research Foundation of State University of New York, New York, N.Y.

[21] Appl. No.: 87,423

[22] Filed: Jul. 2, 1993

[51] Int. Cl.$^6$ ............................ C07K 7/06; A61K 38/08
[52] U.S. Cl. .......................... 514/17; 514/18; 530/328; 530/329; 530/330
[58] Field of Search ........................ 530/328, 329, 530/330; 514/17, 18

OTHER PUBLICATIONS

Vu, T-K, et al. "Molecular Cloning of a Functional Thrombin Receptor Reveals a Novel Proteolytic Mechanism of Receptor Activation, " Cell, 64, pp. 1057–1068 (1991).
Vasallo, R., et al. "Structure—function Relationships in the Activation of Platelet Thrombin Receptors by Receptor–derived Peptides, " J. Biol. Chem., 267, pp. 6081–6085 (1992).
Hui, K., et al. "Minimal Sequence Requirement of Thrombin Receptor Agonist Peptide, " Biochem. Biophys, Res. Commun., 184, pp. 790–796 (1992).
Sabo, T., et al. "Structure–Activity Studies of the Thrombin Receptor Activating Peptide," Biochem. Biophys. Res. Commun., 188, pp. 604–610 (1992).
Scarborough, R., et al. "Tethered Ligand Agonist Peptides, " J. Biol. Chem., 267, pp. 13146–13149 (1992).
Coller, B., et al. "Thrombin Receptor Activating Peptides: Importance of the N–Terminal Serine and Its Ionization State As Judged by pH Dependence, Nuclear Magnetic Resonance Spectroscopy, and Cleavage by Aminopeptidase M, " Biochem., 31, 11713–20 (1992).
Nose, T., et al. "Enhancement of Thrombin Receptor Activation by Thrombin Receptor–Derived Heptapeptide with Para–Fluorophenylalanime in Place of Phenylalanine, " Biochem. Biophys. Res. Commun., 193, 694–699 (1993).
Chao, B., et al. "Essential Groups in Synthetic Peptides for Activation of the Platelet Thrombin Receptor, " Biochem., 31, 6175–6178 (1992).
Ahmad, S. and Ward, P. "Role of Aminopeptidase Activity in the Regulation of the Pressor Activity of Circulating Angiotensins, " J. Pharmacol. Exp. Ther., 252, 643–650 (1990).
Look, A., et al. "Human Myeloid Plasma Membrane Glycoprotein CD13 (gp150) is Identical to Aminopeptidase M., " J. Clin. Invest., 83, 1299–1307 (1989).
Ward, P., et al. "Metabolism of Vasoactive Peptides by Plasma and Purified Renal Aminopeptidase M., " Biochem Pharmacol., 40, 1725–1732 (1990).
Palmieri, F., et al. "Metabolism of Vasoactive Peptides by Vascular Endothelium and Smooth Muscle Aminopeptidase M., " Biochem. Pharmacol. 38, 173–180 (1989).
Vu, T–K., et al. "Domains Specifying Thrombin–Receptor Interaction, " Nature, 353, 674–677 (1991).
Beer, J., et al. "Immobilized Arg–Gly–Asp (RGD) Peptides of Varying Lengths as Structural Probes of the Platelet Glycoprotein IIb/IIIa Receptor, " Blood 79, 117–128 (1992).

*Primary Examiner*—Jill Warden
*Assistant Examiner*—Carol A. Salata
*Attorney, Agent, or Firm*—Hoffmann & Baron

[57] ABSTRACT

A peptide ligand analogue of peptide ligands derived from thrombin-cleaved thrombin receptor site on platelets resists inactivation by aminopeptidase M by substituting the β-amino acid isoserine for the N-terminal serine of the peptide ligand.

4 Claims, 3 Drawing Sheets

Fig. 4A Thrombin Receptor

Fig. 4B ..NATLDPR/SFLLRNPNDKYE.. Thrombin Cleavage Site

SFLLRNPNDKYE.. (new N-terminus)

Fig. 4C SFLLRNPNDKYE.. (tethered ligand) Activation

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 14 Amino Acids
        ( B ) TYPE: Amino Acid
        ( C ) TOPOLOGY: Linear     ( i i ) MOLECULE TYPE: Peptide     ( v ) FRAGMENT TYPE: N-terminal Fragment     ( x i ) SEQUENCE DESCRIPTION: SEQ ID. NO:1:

```
Ser Phe Leu Leu Arg Asn Pro Asn Asp Lys Tyr Glu Pro Phe
 1               5                  10
```

( 2 ) INFORMATION FOR SEQ ID NO:2:

( i ) SEQUENCE CHARACTERISTICS:
        ( A ) LENGTH: 6 Amino Acids
        ( B ) TYPE: Amino Acid
        ( C ) TOPOLOGY: Linear     ( i i ) MOLECULE TYPE: Peptide     ( v ) FRAGMENT TYPE: N-terminal Fragment     ( i x ) FEATURE:
        ( A ) NAME/KEY: Modified-Site
        ( B ) LOCATION: 1
        ( D ) OTHER INFORMATION: /Note ="isoserine,
            2,3- diaminopropanoate or derivatives thereof
            having nucleophilic substituents"

-continued

```
    ( i x ) FEATURE:
            ( A ) NAME/KEY: Modified-Site
            ( B ) LOCATION: 2
            ( D ) OTHER INFORMATION: /Note ="a hydrophobic amino
                    acid having a cyclic or aromatic group."

( i x ) FEATURE:
            ( A ) NAME/KEY: Modified-Site
            ( B ) LOCATION: 3
            ( D ) OTHER INFORMATION: /Note ="a hydrophobic amino
                    acid."

( i x ) FEATURE:
            ( A ) NAME/KEY: Modified-Site
            ( B ) LOCATION: 4
            ( D ) OTHER INFORMATION: /Note ="a hydrophobic amino
                    acid."

( i x ) FEATURE:
            ( A ) NAME/KEY: Modified-Site
            ( B ) LOCATION: 5
            ( D ) OTHER INFORMATION: /Note ="an amino acid."

( i x ) FEATURE:
            ( A ) NAME/KEY: Modified-Site
            ( B ) LOCATION: 6
            ( C ) OTHER INFORMATION: /Note ="carboxyl, carboxamide,
                    at least one amino acid or a moiety which enhances
                    solubility or cell penetrating ability."

( x i ) SEQUENCE DESCRIPTION: SEQ ID NO:2:

Xaa  Xaa  Xaa  Xaa  Xaa  Xaa
    1                   5

( 2 ) INFORMATION FOR SEQ ID NO:3:

( i ) SEQUENCE CHARACTERISTICS:
            ( A ) LENGTH: 5 Amino Acids
            ( B ) TYPE: Amino Acid
            ( D ) TOPOLOGY: Linear ( i x ) FEATURE:
            ( A ) NAME/KEY: Modified-Site
            ( B ) LOCATION: 1
            ( C ) OTHER INFORMATION: /Note ="iso-Ser"

( x i ) SEQUENCE DESCRIPTION: SEQ ID NO:3:

Xaa  Phe  Leu  Leu  Arg
    1                   5

( 2 ) INFORMATION FOR SEQ ID NO:4:

( i ) SEQUENCE CHARACTERISTICS:
            ( A ) LENGTH: 6 Amino Acids
            ( B ) TYPE: Amino Acid
            ( D ) TOPOLOGY: Linear ( i x ) FEATURE:
            ( A ) NAME/KEY: Modified-Site
            ( B ) LOCATION: 1
            ( D ) OTHER INFORMATION: /Note ="iso-Ser"

( x i ) SEQUENCE DESCRIPTION: SEQ ID NO:4:

Xaa  Phe  Leu  Leu  Arg  Asn
    1                   5

( 2 ) INFORMATION FOR SEQ ID NO:5:

( i ) SEQUENCE CHARACTERISTICS:
            ( A ) LENGTH: 21 Amino Acids
            ( B ) TYPE: Amino Acid
            ( C ) TOPOLOGY: Linear
```

( i i ) MOLECULE TYPE: Peptide ( v ) FRAGMENT TYPE: Internal Fragment ( x i ) SEQUENCE DESCRIPTION:SEQ ID NO:5:

```
Asn Ala Thr Leu Asp Pro Arg Ser Phe Leu Leu
1               5                   10
Arg Asn Pro Asn Asp Lys Tyr Glu Pro Phe
15              20
```

( 2 ) INFORMATION FOR SEQ ID NO:6:

( i ) SEQUENCE CHARACTERISTICS:
        ( A ) LENGTH: 6 Amino Acids
        ( B ) TYPE: Amino Acid
        ( D ) TOPOLOGY: Linear     ( i i ) MOLECULE TYPE: Peptide     ( v i ) FRAGMENT TYPE: N-Terminal Fragment     ( i x ) FEATURE:
        ( A ) NAME/KEY: Modified-Site
        ( B ) LOCATION: 1
        ( D ) OTHER INFORMATION: /Note ="D-Ser"

( x i ) SEQUENCE DESCRIPTION: SEQ ID NO:6:

```
Xaa Phe Leu Leu Arg Asn
1               5
```

( 2 ) INFORMATION FOR SEQ ID NO:7:

( i ) SEQUENCE CHARACTERISTICS:
        ( A ) LENGTH: 6 Amino Acids
        ( B ) TYPE: Amino Acid
        ( D ) TOPOLOGY: Linear     ( i i ) MOLECULE TYPE: Peptide     ( i x ) FEATURE:
        ( A ) NAME/KEY: Modified-Site
        ( B ) LOCATION: 1
        ( D ) OTHER INFORMATION: /Note ="racemic (R,S)isoserine"

( x ) SEQUENCE DESCRIPTION: SEQ ID NO:7:

```
Xaa Phe Leu Leu Arg Asn
1               5
```

( 2 ) INFORMATION FOR SEQ ID NO:8:

( i ) SEQUENCE CHARACTERISTICS:
        ( A ) LENGTH: 6 Amino Acids
        ( B ) TYPE: Amino Acid
        ( D ) TOPOLOGY: Linear     ( i x ) FEATURE:
        ( A ) NAME/KEY: Modified-Site
        ( B ) LOCATION: 1
        ( D ) OTHER INFORMATION: /Note ="2,3-diaminopropanoyl"

( x i ) SEQUENCE DESCRIPTION: SEQ ID NO:8:

```
Xaa Phe Leu Leu Arg Asn
1               5
```

( 2 ) INFORMATION FOR SEQ ID NO:9:

( i ) SEQUENCE CHARACTERISTICS:
        ( A ) LENGTH: 6 Amino Acids
        ( B ) TYPE: Amino Acid
        ( D ) TOPOLOGY: Linear

```
       ( i x ) FEATURE:
                ( A ) NAME/KEY: Modified-Site
                ( B ) LOCATION: 1
                ( D ) OTHER INFORMATION: /Note ="2,3-dihydroxypropanoyl"

( x i ) SEQUENCE DESCRIPTION: SEQ ID NO:9:

Xaa  Phe  Leu  Leu  Arg  Asn
          1                   5

( 2 ) INFORMATION FOR SEQ ID NO:10:

( i ) SEQUENCE CHARACTERISTICS:
                ( A ) LENGTH: 6 Amino Acids
                ( B ) TYPE: Amino Acid
                ( D ) TOPOLOGY: Linear ( i x ) FEATURE:
                ( A ) NAME/KEY: Modified-Site
                ( B ) LOCATION: 2
                ( D ) OTHER INFORMATION: /Note ="p-benzoylphenylalanine"

( x i ) SEQUENCE DESCRIPTION: SEQ ID NO:10:

Ser  Xaa  Leu  Leu  Arg  Asn
          1                   5

( 2 ) INFORMATION FOR SEQ ID NO:11:

( i ) SEQUENCE CHARACTERISTICS:
                ( A ) LENGTH: 11 Amino Acids
                ( B ) TYPE: Amino Acid
                ( D ) TOPOLOGY: Linear ( i x ) FEATURE:
                ( A ) NAME/KEY: Modified-Site
                ( B ) LOCATION: 1
                ( D ) OTHER INFORMATION: /Note ="D-Ser"

( x i ) SEQUENCE DESCRIPTION: SEQ ID NO:11:

Xaa  Phe  Leu  Leu  Arg  Asn  Pro  Asn  Asp  Lys  Tyr
          1                   5                         1 0
```

PEPTIDASE RESISTANT THROMBIN RECEPTOR PEPTIDE LIGAND

This invention was made with Government support under grant number HL19278 awarded by the National Institutes of Health. The Government has certain rights in the invention.

BACKGROUND OF THE INVENTION

1. Field of the Invention

The invention relates to the substitution of an N-terminal amino acid in a peptide ligand of the thrombin receptor on platelets thereby conferring resistance to enzyme cleavage of the ligand and thus avoiding inactivation of platelet aggregating activity mediated by the ligand.

2. Description of the Related Art

Hemostasis is a complex process involving blood coagulation which proceeds along an extrinsic pathway or an intrinsic pathway. In both pathways, the final steps involve the formation of the enzyme thrombin which catalyzes the conversion of fibrinogen plasma protein into insoluble fibrin. In the intrinsic pathway, platelets adhere to a ruptured blood vessel and begin to clump. They then serve to accelerate the generation of the enzyme thrombin that causes blood to clot.

Thrombin also causes more platelets to clump and facilitates even more thrombin generation. Thrombin is a potent platelet agonist in vitro. It produces platelet shape change, aggregation and release of granule contents.

Thrombin's importance has stimulated research on the mechanism by which it activates platelets. A functional thrombin receptor has been identified on the surface membrane of platelets by Vu et al., Cell 64, 1057–1068 (1991).

Thrombin cleavage of the receptor produces a new amino terminal (SFLLRNPNDKYEPF, T-14) SEQ ID NO:1 tethered ligand peptide on the platelet surface. The peptide ligand is able to aggregate gel-filtered platelets directly. Therefore, thrombin induces platelet activation, at least in part, by cleaving the receptor on platelets, which permits the new amino terminus to function as a tethered ligand, interacting with another region of the receptor to induce activation signal(s).

Subsequent studies have shown that peptide ligands containing just the first five or six amino acids of T-14 are also active. (Vassallo et al. J. Biol. Chem. 267, 6081–6085 (1992); Hui et al., Biochem. Biophys. Res. Commun. 184, 790–796 (1992); Sabo et al., Biochem. Biophys. Res. Commun. 188, 604–610 (1992); Scarborough et al., J. Biol. Chem. 267, 13146–13149 (1992). Most groups found that the 6-mer is more active than the 14-mer.

The importance of a positive charge on the N-terminal serine was suggested from studies by the inventors herein, Coller et al., Biochem. 31, 11713–11720 (1992), and by others. Coller et al. and others also showed that acetylation of the amino terminus leads to loss of peptide activity and identified a correlation between peptide activity and the positive charge on the N-terminal serine. Coller et al., Id., and others (Vassallo et al., J. Biol. Chem. 267, 6081–6085 (1992); Scarborough et al., J. Biol. Chem. 267, 13146–13149 (1992)) showed that omitting the N-terminal serine of the ligand leads to loss of activity. The hydroxyl moiety of the N-terminal serine is not crucial for activity, however, since peptides in which alanine substitutes for serine retain substantial activity as shown by Sabo et al., Biochem. Biophys. Res. Commun. 188, 604–610 (1992); and Chao, et al., Biochem 31, 6175–6178 (1992).

Finally, Coller et al., Biochem. 31, 11713–11720 (1992) demonstrated that aminopeptidase M which is naturally occurring in plasma and serum and on endothelial cells, rapidly cleaves the N-terminal serine from peptide ligands, leading to loss of their ability to activate thrombin receptors. At micromolar concentrations of the peptide, the cleavage is rapid enough in platelet-rich plasma (PRP) to affect the platelet aggregation response. Even at millimolar concentrations, incubation with 50% plasma at 37° C. leads to significant cleavage of the N-terminal serine by aminopeptidase M and loss of platelet aggregating activity.

Aminopeptidase M is the major enzyme responsible for the ability of plasma to cleave N-terminal neutral/basic amino acids from low molecular weight peptides (Ward et al., Biochem. Pharmacol. 40, 1725–1732 (1990); Ahmad and Ward, J. Pharmacol. Exp. Ther. 252, 643–650 (1990). Endothelial cells, smooth muscle cells, leukocytes, monocytes and other cells are known to contain aminopeptidase M (Look et al. J. Clin. Invest. 83, 1299–1307 (1989); Palmieri et al., Biochem. Pharm. 38, 173–180 (1989); Semenza, Rev. Cell. Biol. 2, 255–313 (1986)).

The rapid degradation and inactivation of the peptide ligand in the presence of plasma and serum makes it difficult to assess dose-response relationships precisely. In addition, an appreciation of the aminopeptidase cleavage and inactivation process raises the possibility that some of the observed effects of the peptides have resulted from only brief receptor activation, since dissociation of the peptide from the receptor may occur rapidly as the concentration of intact fluid-phase peptide decreases.

Although aminopeptidase M can be inhibited by compounds such as amastatin, leading to enhanced platelet aggregation responses of PRP to peptide ligand (Coller et al., Biochem. 31, 11713–11720 (1992)), amastatin and other aminopeptidase M inhibitors may have unknown effects on cells or plasma proteins. Acetylation of the N-terminus is the traditional method for producing a peptide that resists cleavage by aminopeptidase M, but acetylation of this ligand eliminates receptor activator activity.

Accordingly, it is an object of the invention to provide a means to prevent inactivation of the thrombin receptor peptide ligand.

It is a further object of the invention to provide a thrombin receptor peptide ligand that retains substantial functional activity but is resistant to cleavage by aminopeptidase M.

It is yet another object to provide a non-naturally occurring peptide that activates platelet aggregation.

SUMMARY OF THE INVENTION

The invention provides a method for inhibiting the enzymatic action of aminopeptidase M on a peptide residue thus allowing the peptide to retain activity for platelet aggregation.

The peptide of the invention includes an isoserine or other residue substituted for the wild type serine residue at the N-terminus. Therefore, a peptide of formula I is provided as follows:

$R_1$ -$R_2$-$R_3$-$R_4$-$R_5$-Z SEQ ID NO:2 formula I wherein:

$R_1$ is isoserine, 2,3-diaminopropanoate, 2,3-dihydroxypropanoate or derivatives thereof having nucleophilic substituents $R_2$ is a hydrophobic amino acid having a cyclic or aromatic group $R_3$ is a hydrophobic amino acid $R_4$ is a hydrophobic amino acid $R_5$ is an amino acid Z is carboxyl, carboxamide, at least one amino acid or a moiety which enchances solubility or cell penetrating ability of formula I.

Preferred peptides of formula I are (iso-Ser)-Phe-Leu-Leu-Arg-$NH_2$ SEQ ID NO:3 or (iso-Ser)-Phe-Leu-Leu-Arg-Asn-$NH_2$ SEQ ID NO:4. Most preferred is the 6-mer.

A method for resisting inactivation of thombin receptor activation peptide by aminopeptidase M comprises administering an effective amount of a polypeptide compound having formula I.

Preferred embodiments of the method utilize formula I having the sequences (iso-Ser)-Phe-Leu-Leu-Arg-$NH_2$ SEQ ID NO:3 or (iso-Ser)-Phe-Leu-Leu-Arg-Asn-$NH_2$ SEQ ID NO:4. Most preferred is the 6 -mer.

DETAILED DESCRIPTION OF THE INVENTION

The peptides of the invention are characterized by the ability to resist degradation by aminopeptidase M while the peptides retain their activity in inducing platelet aggregation. Therefore the invention aids blood clotting and finds utility, as a non-limiting example, in topical application to injured areas of the body where local clotting is desired. In addition, since thrombin is mitogenic for fibroblasts, peptides that activate the thrombin receptor may enhance wound healing.

The nomenclature used to describe peptides of the present invention follows the conventional practice in which the amino group is presented to the left and the carboxy group to the right of each amino acid residue. The term residue with reference to an amino acid means a radical derived from the corresponding α- or β- amino acid by eliminating the hydroxyl of the carboxy group and one hydrogen of the α- or β- amino group.

The abbreviations used for designating the amino acids are single letter designations or three letter designations according to the following standard abbreviations and 37 C.F.R. §1.822:

| Amino acid | Three-letter abbreviation | One-letter abbreviation |
|---|---|---|
| alanine | Ala | A |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |
| other | Xaa | |

For instance, S, F, L, L, R, N, P, N, D, K, Y, E, P, F or Ser, Phe, Leu, Leu, Arg, Asn, Pro, Asn, Asp, Lys, Tyr, Glu, Pro, Phe represent the residues of L-serine, L-phenylalanine, L-leucine, L-leucine, L-arginine, L-asparagine, L-proline, L-asparagine, L-aspartic acid, L-lysine, L-tyrosine, L-glutamic acid, L-proline and L-phenylalanine.

The amino acids possess the L-configuration, except isoserine, unless otherwise indicated, and the starting materials for providing the amino acid residues, usually the corresponding N-α protected amino acids, are commercially available or can be prepared by conventional methods. The basic amino group of amino acids can bind a proton from solution and become a cation; the acidic carboxyl can release a proton into solution and become an anion. Therefore, since amino acids are ionic, they can be prepared as salts.

The term isoserine refers to an isomer of serine having the formula $NH_2CH_2CHOHCOOH$ and which also can be termed 2-hydroxy beta alanine or 3-amino-2-hydroxypropanoic acid. The C-2 position of isoserine is chiral and isoserine which we first employed is described as racemic, that is, an equal mixture of D and L isomers. However, the D and L terminology is somewhat ambiguous for isoserine.

Another nomenclature which is more accurately used because it is unambiguous when describing absolute configuration of unnatural substituents in this application is (R,S). L-serine is said to have the (S)-configuration at the active carbon. We have tested racemic iso-Ser, that is, iso-serine which has the (R,S) configuration at C-2. The (2R) and (2S) isomers of the preferred embodiment may have different activities.

Most naturally occurring amino acids are α-amino acids meaning that an amino group (—$NH_2$) and a carboxyl group (—COOH) are attached to the same carbon atom. The invention makes use of a non-naturally occurring β-amino acid, isoserine. The use of the β-amino acid still results in a polypeptide having biological activity for platelet activation.

In the peptides, the end to the left is called the N-terminus and the end to the right is called is the C-terminus. When C-terminus is followed in common usage, by a —NH$_2$, this indicates C-terminal amidations. This convention is commonly employed when other amino acid residues may follow at this end. This convention is used in the present application.

Figures 4A, 4B, 4C:
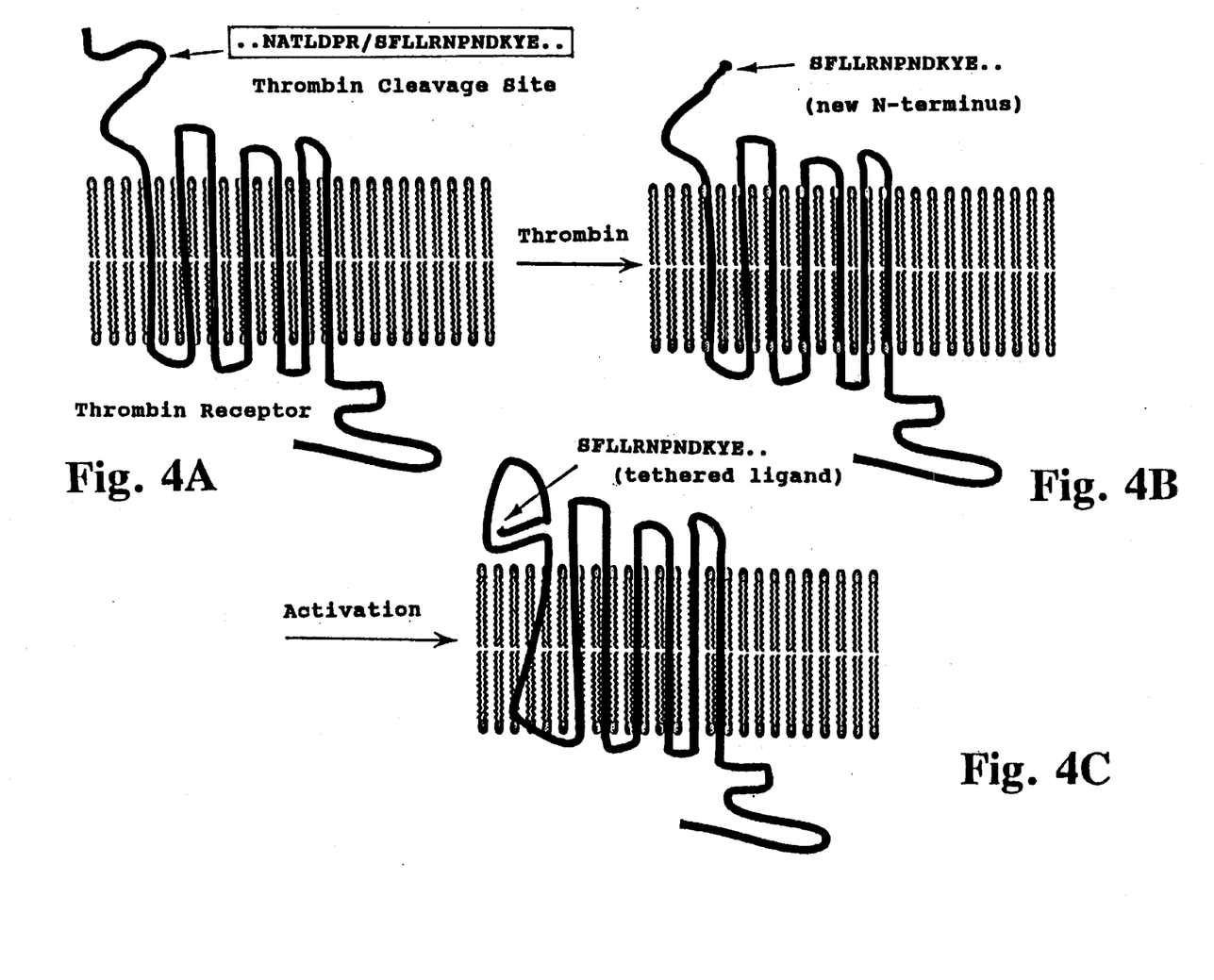
FIGS. 4A–C are representations of the thrombin receptor site before and after cleavage and after conformational change.

The amino acid sequence of the thrombin receptor site on platelets has been identified by Vu, et al., Cell 64, 1057–1068 (1991). The cDNA contains an open reading frame of 425 amino acids and a hydropathy plot suggests the presence of seven transmembrane domains. The thrombin receptor site with transmembrane domains and the results of thrombin cleavage are pictorially illustrated in FIG. 4. FIG. 4A illustrates the thrombin receptor with its seven transmembrane domains. FIG. 4B illustrates the tethered ligand after thrombin cleavage. FIG. 4C illustrates a conformational change upon ligand binding that activates the thrombin receptor and lends to platelet aggregation. The putative thrombin cleavage site was identified between R41 and S42 as follows -continued
SCHEME I The naturally-occurring L-serine residue is represented by formula a. The nearly inactive D-serine is represented by formula b.

Thrombin cleavage between R41 and S42 results in a tethered ligand peptide having an N-terminal serine. Plasma aminopeptidase M can cleave the N-terminal serine from the tethered ligand peptides derived from the cleaved thrombin receptor site, leading to the total loss of platelet activating activity. At micromolar peptide ligand concentrations, the inactivation occurs rapidly enough to affect platelet aggre-

| N | A | T | L | D | P | R/ | S | F | L | L | R | N | P | N | D | K | Y | E | P | F | SEQ ID NO: 5 |
|---|---|---|---|---|---|----|---|---|---|---|---|---|---|---|---|---|---|---|---|---|---|
| 35 | 36 | 37 | 38 | 39 | 40 | 41 | 42 | 43 | 44 | 45 | 46 | 47 | 48 | 49 | 50 | 51 | 52 | 53 | 54 | 55 | |

A 14 amino acid peptide mimicking the new amino terminus

SFLLRNPNDKYEPF SEQ ID NO:1 T-14

S42-F55 is able to aggregate gel-filtered platelets directly. Peptide ligands containing just the first five or six amino acids of T-14 are also active. The D- and L-serine peptides are shown in Scheme I.

SCHEME I

D-SFLLRN SEQ ID NO:6
(inactive)

gation in platelet-rich plasma. Thus, after exposure to either plasma or serum, the concentration of peptide ligand changes rapidly, making dose-response and long-term experiments difficult to perform and interpret.

To overcome this problem, a peptide ligand analogue has been produced that resists aminopeptidase cleavage and inactivation by making certain substitutions for the N-terminal serine.

The stereochemistry of isoserine and serine may be represented as follows:

L-Serine
(S)-2-amino-3-hydroxy-propanoic acid

D-Serine
(R)-2-amino-3 hydroxy-propanic acid (R)-isoSerine
(R)-2-hydroxy-3-amino-propanic acid (S)-isoSerine
(S)-2-hydroxy-3-amino-propanoic acid

(R) and (S) are unambiguous but arbitrary designations based on the arrangement in space of the groups attached to the central carbon atom. For Ser, the priorities are N>CO$_2$>C-O; for iso-Ser, the priorities are O>C-N>CO$_2$.

Residues which may be used for R$_1$ in the invention include (R)-isoserine ((R)-2-hydroxy-3-aminopropanoic acid), (S)-isoserine ((S)-2-hydroxy-3-aminopropanoic acid), 2,3-diaminopropanoate and 2,3-dihydroxypropanoate. The residues for R$_1$ may have nucleophilic substituents such as OH, NH, SH, and acyl. Preferred serine analogues for R$_1$ are (R,S)isoserine.

A peptide of formula I containing racemic isoserine is shown in Scheme II.

SCHEME II racemic iso-SFLLRN SEQ ID NO:7
(one or both isomers are active)

isoserine     isoserine

The non-naturally occurring (R) and (S) isoserine analogues are represented by formulas c and d.

Other residues for $R_1$ are shown in formula e and f.

2,3-diamino-
propanoylFLLRN SEQ ID NO:8

2,3-diamino-
propanoic acid 2,3-dihydroxy-
propanoylFFLRN SEQ ID NO:9

2,3-dihydroxy-
propanoic acid

Studies have suggested that the Phe residue at $R_2$ is important (Chao et al., Biochem. 31, 6175–6178 (1992)). It has been theorized that a properly oriented $R_2$ Phe-phenyl group is crucial for a necessary hydrophobic interaction with thrombin receptor and that the receptor has a specific binding site for this phenyl group. Nose et al., Biochem Biophys. Res. Commun. 193,694–699 (1993) found that replacement of Phe-2 by fluorophenylalanine enhanced activation of the thrombin receptor.

In the peptide ligand of formula I, $R_2$ may be any hydrophobic amino acid residue having a cyclic or aromatic group. Naturally-occurring amino acids of this type include phenylalanine and tryptophan.

Non-naturally occurring analogues of phenylalanine may include non-naturally occurring substitutions such as p-benzoyl, p-fluoro-, p-methyl, p-methoxy and the like. A preferred non-naturally occurring amino acid residue for $R_2$, p-benzoylphenylalanine, is represented by formula h in Scheme III below:

SCHEME III formula h
p-benzoylphenylalanine

SBLLRN SEQ ID NO:10
(B = p-Benzoylphenylalanine

Non-naturally occurring analogues of phenylalanine are represented by formula II:

X = fluorine, methyl or benzoyl

Preferred amino acids for $R_2$ are phenylalanine, p-benzoylphenylalanine, p-fluorophenylalanine and p-methylphenylalanine. The X group may also be any hydrophobic group, and the X group may be located in the ortho or meta position on the benzene ring.

$R_3$ may be any hydrophobic amino acid such as alanine, phenylalanine, glycine, isoleucine, leucine, methionine, proline, serine, threonine, tryptophan and valine. Preferred are leucine, phenylalanine and alanine. Most preferred is leucine.

R₄ may be any hydrophobic amino acid such as those listed for R₃. Preferred are leucine and alanine. Most preferred is leucine.

$R_5$ may be any amino acid e.g. alanine, arginine, asparagine, aspartic acid, cysteine, glutamine, glutamic acid, glycine, histidine, isoleucine, leucine, lysine, methionine, phenylalanine, proline, serine, threonine, typtophan, tyrosine and valine, preferably one which is basic. Preferred are arginine and alanine. Most preferred is arginine.

Z may be carboxy, carboxamide, an amino acid sequence containing at least one amino acid residue beginning at the N-terminal of the sequence Asn-Pro-Asn-Asp-Lys-Tyr-Glu-Pro-Phe-NH₂ amino acids 13 to 21 of SEQ ID NO:5, any other amino acid or a moeity which enhances the solubility or cell penetrating ability of formula I. Such moieties are known in the art and include, e.g., lipids, steroids, long chain amines such as decylamine, sugars such as conjugates of glucosamine, glucuronic acid, etc.

The peptide (iso-Ser)-Phe-Leu-Leu-Arg-Asn-NH₂ SEQ ID NO:7 was prepared by first synthesizing Phe-Leu-Leu-Arg-Asn-NH₂ amino acids 2 to 6 of SEQ ID NO:7 on an automated peptide synthesizer using t-BOC chemistry and then adding racemic t-BOC isoserine manually. The (iso-Ser)-Phe-Leu-Leu-Arg-Asn-NH₂ SEQ ID NO:7 proved to be substantially active as compared with the naturallyoccurring peptide. It is possible that only one of the diasteroisomers of (iso-Ser)-Phe-Leu-Leu-Arg-Asn-NH₂ SEQ ID NO:7 is active.

Meanwhile, when incubated with plasma at 37° C., the naturally occurring peptide underwent progressive degradation resulting in almost total (96%) peptide cleavage after about two hours. Indeed, with the naturally-occurring peptide, platelet aggregating activity decreased within 15 minutes and was nearly lost at 60 minutes. In contrast, (iso-Ser)-Phe-Leu-Leu-Arg-Asn-NH₂ SEQ ID NO:7 did not undergo identifiable cleavage even at 45 minutes; at two hours, only about 17% cleavage occurred and the platelet aggregating activity remained unchanged for at least two hours. Therefore, the isoserine substituted peptide resists cleavage and inactivation by plasma aminopeptidase M. The stability of the isoserine substituted peptide improves studies conducted in plasma or serum-containing media. In addition, the substituted peptide fragment can be added exogenously to supplement the action of the naturally occurring peptide and enhance local coagulation at the site of an injury.

The invention will be illustrated by the following non-limiting examples.

EXAMPLE 1

Peptides: The 11 amino acid peptide Ser-Phe-Leu-Leu-Arg-Asn-Pro-Asn-Asp-Lys-Tyr (T-11) amino acids 1 to 11 of SEQ ID NO:1, representing the amino acid sequence 42-52 from the thrombin receptor; the same peptide containing D-serine instead of L-serine ((dS)T-11); and the 6 amino acid peptide Ser-Phe-Leu-Leu-Arg-Asn amino acids 8 to 13 of SEQ ID NO:5 (representing amino acids 42-47), were synthesized by conventional methods of peptide synthesis. The peptides were synthesized as C-terminal amides on an automated peptide synthesizer (Applied Biosystems 430A, Foster City, Calif.) using t-Boc Chemistry, 4-methylbenzhydrylamine resins, and N-methylpyrrolidone as the coupling solvent as described by Beer et al., Blood 79, 117–128 (1992). The protecting groups were β-benzyl ester for aspartic acid, benzyl for serine, 2-bromobenzyloxycarbonyl for tyrosine, 2-chlorobenzyloxycarbonyl for lysine, and tosyl for arginine. Arginine, asparagine, tyrosine and selected proline and phenylalanine residues were double-coupled. Dimethylsulfide and anisole were included in all of the hydrogen fluoride cleavage solutions. Peptides were assessed by reverse-phase high performance liquid chromatography (HPLC) and selected peptides were purified by this technique. The mass of selected peptides was determined by fast atom bombardment mass spectrometry as described by Beer et al., Blood 79, 117–128 (1992).

A peptide in which isoserine was substituted for the N-terminal serine in Ser-Phe-Leu-Leu-Arg-Asn amino acids 1 to 6 of SEQ ID NO:1, that is (iso-Ser)-Phe-Leu-Leu-Arg-Asn SEQ ID NO:7, was prepared by first synthesizing the peptide Phe-Leu-Leu-Arg-Asn amino acids 2 to 6 of SEQ ID NO:7 by the automated method and then manually adding the t-butyloxycarbonyl (t-Boc) protected racemic isoserine in dichloromethane + dimethyl formamide (2:1) to the peptide on the resin using 1-hydroxybenzotriazole to activate the isoserine and N,N'-diisopropylcarbodiimide to couple it to the peptide. The peptide was then cleaved from the resin with hydrogen fluoride solution and used directly as a mixture of the diastereoisomers. HPLC analysis demonstrated that about 68% of the absorbance at 220 nm was in the major peak for the (iso-Ser)-Phe-Leu-Leu-Arg-Asn SEQ ID NO:7 and T-11 amino acids 1 to 11 of SEQ ID NO:1 peptides, 52% was in the major peak for the (D-Ser)T-11 peptide SEQ ID NO:11, and about 75% was in the major peak for the Ser-Phe-Leu-Leu-Arg-Asn amino acids 1 to 6 of SEQ ID NO:1 peptide. The peptide concentrations reported in results were corrected for these values.

EXAMPLE 2

Platelet Aggregation. Platelet Rich Plasma (hereinafter "PRP") was obtained from human blood anticoagulated with sodium citrate (0.01 volume of 40% trisodium citrate) or acid-citrate-dextrose (hereinafter "ACD") solution A (ACD-A; 8.5 mL of blood: 1.5 mL of ACD-A) by centrifugation at 700 g for 3.5 min. at 22° C. Platelet-poor plasma (hereinafter "PPP") was obtained by centrifuging the PRP at 2000g for 8 min. at 22° C. The pH of the citrated PRP after preparation was about 7.7 whereas the pH of the ACD-A PRP was about 7.0. The pH of the PRP was adjusted, when necessary with 1M NaOH or 1M HCl and maintained at about 7.70. Platelet aggregation was performed in a dual-channel aggregometer (Chronolog, Hayertown, Pa.) using matched stir bars.

Dose Response of Peptide-Induced Aggregation. Citrated platelet-rich plasma (PRP; 307,000 platelets/μl, pH 7.0; 0.45 ml) was stirred in a cuvette at 37° C. and then 10ml of Ser-Phe-Leu-Leu-Arg-Asn-Pro-Asn-Asp-Lys-Tyr (T-11) amino acids 1 to 11 of SEQ ID NO:1, (D-Ser)-Phe-Leu-Leu-Arg-Asn-Pro-Asn-Asp-Lys-Tyr ((DS)T-11) SEQ ID NO:11, Ser-Phe-Leu-Leu-Arg-Asn amino acids 1 to 6 of SEQ ID NO:1 or (iso-Ser)-Phe-Leu-Leu-Arg-Asn SEQ ID NO:7 peptide was added to achieve the final concentration as follows: Ser-Phe-Leu-Leu-Arg-Asn-Pro-Asn-Asp-Lys-Tyr amino acids 1 to 11 of SEQ ID NO:1 was added to a maximum concentration of 2.9 μM; (D-Ser)-Phe-Leu-Leu-Arg-Asn-Pro-Asn-Asp-Lys-Tyr SEQ IS NO:11 was added to a maximum concentration of 940 μM; Ser-Phe-Leu-Leu-Arg-Asn amino acids 1 to 6 of SEQ ID NO:1 was added to a maximum concentration of 1.7 μM; (iso-Ser)-Phe-Leu-Leu-Arg-Asn SEQ ID NO:7 was added up to a maximum concentration of 4.9 μM.

Figure 1A:
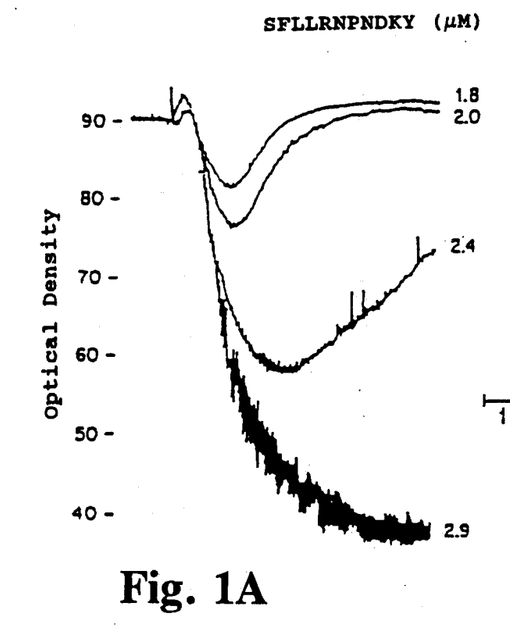
FIGS. 1A–D are graphical comparisons of the dose-response of platelet aggregation induced by T-11 amino acids 1 to 11 of SEQ ID NO:1, (DS)T-11 SEQ ID NO:11, SFLLRN amino acids 1 to 6 of SEQ ID NO:1 and (iso-S)FLLRN SEQ ID NO:7.

A comparison of the dose-response of platelet aggregation induced by T-11 amino acids 1 to 11 of SEQ ID NO:1, (DS)T-11 SEQ ID NO:11, SFLLRN amino acids 1 to 6 of SEQ ID NO:1 and (iso-S)FLLRN SEQ ID NO:7 is shown in FIG. 1A, B, C and D. The results in FIG. 1B demonstrate that the (DS)T-11 SEQ ID NO:11 had only minimal aggregating activity. Even a dose of 940 µM (DS)T-11 SEQ ID NO:11 produced less aggregation activity than 2.9 µM T-11 amino acids 1 to 11 of SEQ ID NO:1. The slope of the late platelet disaggregation phase identifiable in the samples not undergoing maximal aggregation was less steep with (DS)T-11 SEQ ID NO:11 than with T-11 amino acids 1 to 11 of SEQ ID NO:1 at doses giving equivalent peak aggregation response (15 U/min for T-11 amino acids 1 to 11 of SEQ ID NO:1 at 1.8 µM and 5 U/min for (DS)T-11 SEQ ID NO:11 at 680 µM). The reduction in the slope of disaggregation with D-Serine is consistent with a decrease in aminopeptidase M cleavage of the D-serine peptide.

Figure 1B:
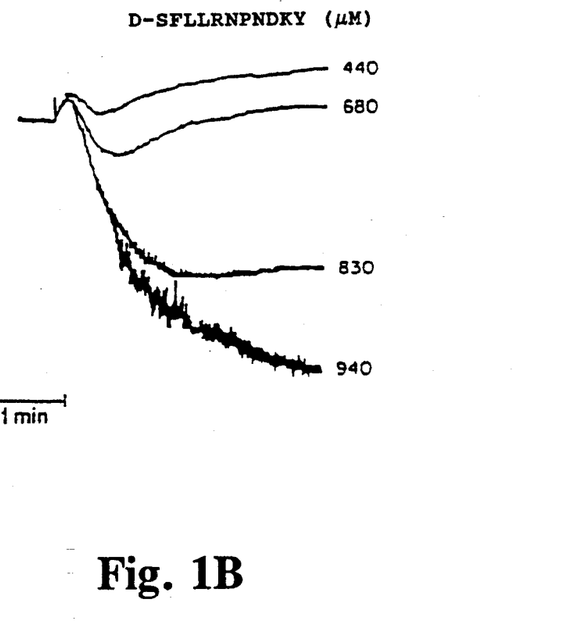
Figure 1C:
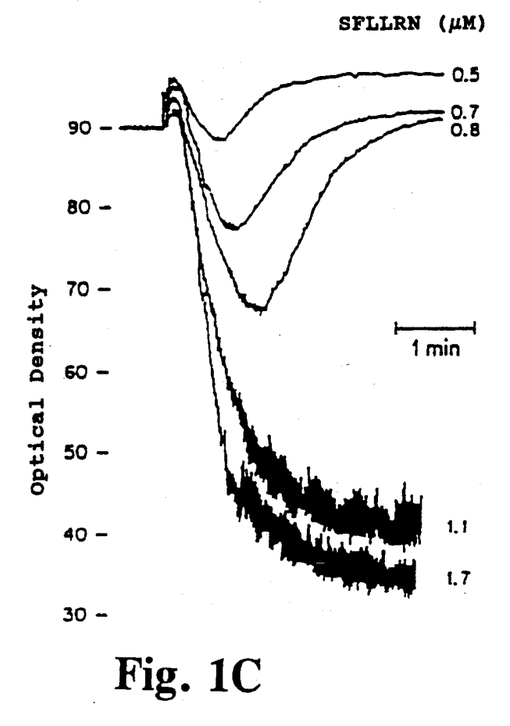
Figure 1D:
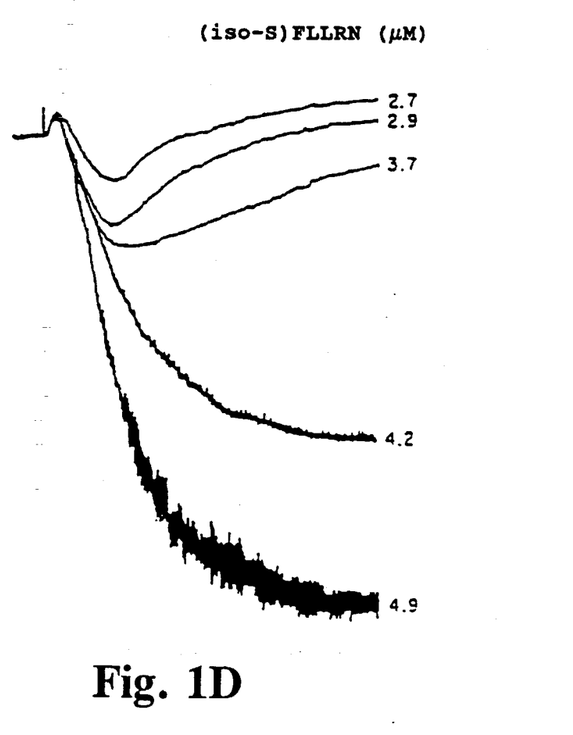

FIG. 1C shows that SFLLRN amino acids 1 to 6 of SEQ ID NO:1 was the most active peptide, requiring ~0.8 µM to achieve half-maximal aggregation. FIG. 1A shows that SFLLRNPNDKY (T-11) amino acids 1 to 11 of SEQ ID NO:1 was similar in potency to (iso-S)FLLRN SEQ ID NO:7 shown in FIG. 1D with half maximal aggregation concentration of ~3.3 and 4.0 µM respectively. DSFLLRNPNDKY SEQ ID NO:11 ((DS)T-11) was only minimally active, being unable to achieve maximal aggregation even at 1.8 µM as shown in FIG. 1B.

These data show that, in accord with previous observations, the 6 amino acid peptide SFLLRN amino acids 1 to 6 of SEQ ID NO:1 was more active than the longer T-11 amino acids 1 to 11 of SEQ ID NO:1, with the former producing half-maximal aggregation at ~0.8 µM and the latter requiring ~2.2 µM as shown in FIG. 1. Aggregation induced by SFLLRN amino acids 1 to 6 of SEQ ID NO:1, like that of T-11 amino acids 1 to 11 of SEQ ID NO:1, demonstrated a steep slope of disaggregation. The (iso-S)FLLRN SEQ ID NO:7 peptide required ~4 µM to achieve half-maximal aggregation. Thus, (iso-S)FLLRN SEQ ID NO:7 has ~15-20% of the platelet activating activity of SFLLRN amino acids 1 to 6 of SEQ ID NO:1. At doses giving equivalent peak aggregation responses, the disaggregation phase slope was less steep with (iso-S)FLLRN SEQ ID NO:7 than with SFLLRN amino acids 1 to 6 of SEQ ID NO:1 (13 U/min for SFLLRN amino acids 1 to 6 of SEQ ID NO:1 at 0.7 µM and 4 U/min for (iso-S)FLLRN SEQ ID NO:7 at 3.7 µM). This also suggest that the (iso-S)FLLRN SEQ ID NO:7 is less readily cleaved by aminopeptidase M.

EXAMPLE 3

Inactivation of Peptide Aggregating Activity by Plasma. We have previously demonstrated that T-11 amino acids 1 to 11 of SEQ ID NO:1 and T-14 SEQ ID NO:1 peptides lost aggregating activity when incubated in plasma due to cleavage of the N-terminal serine by aminopeptidase M; that endothelial cell aminopeptidase M was also able to cleave T-11 amino acids 1 to 11 of SEQ ID NO:1; and that inhibiting aminopeptidase M with amastatin enhanced aggregation induced by T-11 amino acids 1 to 11 of SEQ ID NO:1 but not thrombin. B. Coller et al., Biochemistry 31, 11713–11720 (1992). Additional peptide digestion studies were carried out as follows:

Peptide Digestion Studies. For T-11 amino acids 1 to 11 of SEQ ID NO:1 and (D-Ser)T-11 SEQ ID NO:11 digestions, 0.11 volume of 20 mM peptide in 0.15M NaCl, 0.01 Tris/HCl, pH 7.4, was added to citrated platelet-poor plasma to achieve a final concentration of 2 mM. Samples were incubated for 2 hours at 37° C. and then the plasma proteins were precipitated with 9–10% trichloroacetic acid at 4° C. for at least 30 min. After centrifugation at 12000 g at 22° C. for 3 min., the supernatant was analyzed to determine peptide cleavage by reverse-phase HPLC (C8; Applied Biosystems 300 RP Aquapore; 220×4.6-mm column); elution was with 0.1% trifluoroacetic acid with a 0–60% acetonitrile gradient.

To determine the amino acid sequence of the digestion products of T-11 amino acids 1 to 11 of SEQ ID NO:1 and (D-Ser)T-11 SEQ ID NO:11 and to assess their ability to aggregate platelets, the peptide (2 mM) was incubated with citrated PPP for 2 hours at 37° C., plasma proteins were precipitated with trichloroacetic acid, and the supernatant after centrifugation was both analyzed and fractionated on the analytical reverse-phase column. Peak fractions were dried in a vacuum centrifuge (Speed-Vac, Savant, Farmingdale, N.Y.) and dissolved in either buffer (0.15M NaCl and 0.01 M Tris/HCl, pH 7.4) for aggregation studies or 0.1% trifluoroacetic acid for amino acid analysis. Quantitative amino acid analysis of the peptides was performed with commercial reagents and equipment (Pico-Tag workstation and C-18 Pico-Tag column; Waters-Millipore, Bedford, Mass.). The amino acid sequence could then be inferred from the amino acid content of each peak.

Preincubation of T-11 amino acids 1 to 11 of SEQ ID NO:1 in plasma at 37° C led to progressive loss of platelet aggregating ability. Incubation times as short as 10 min. were sufficient to produce significant inhibition. After 2 hours of incubation of the T-11 amino acids 1 to 11 of SEQ ID NO:1 peptide (2 mM) at 37° C. with platelet-poor plasma, only 34% of the peptide remained intact; in contrast, the (DS)T-11 SEQ ID NO:11 peptide did not undergo any identifiable cleavage under the same conditions (data not shown).

Figure 2A:
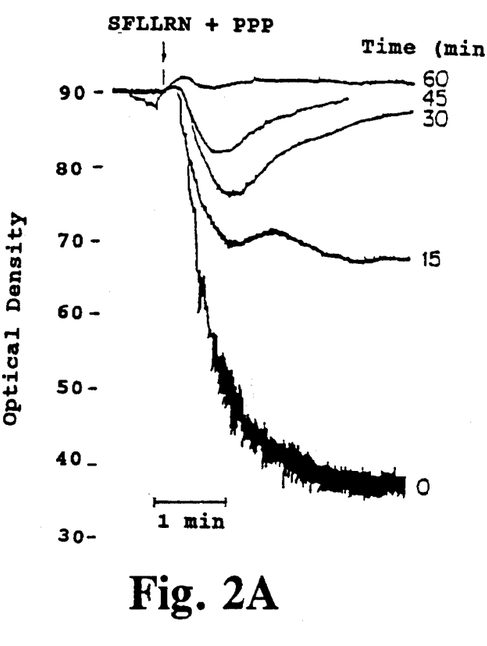
FIGS. 2A and B are graphical comparisons of the effect of incubating SFLLRN amino acids 1 to 6 of SEQ ID NO:1 and (iso-S)FLLRN SEQ ID NO:7 in plasma for various periods of time on the peptides' ability to induce platelet and aggregation.
Figure 2B:
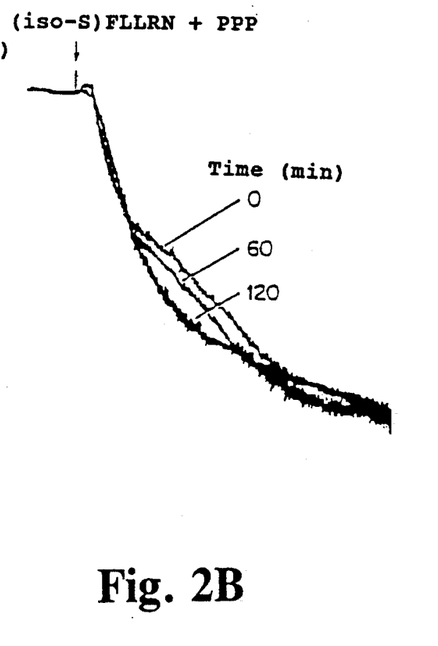

For the Ser-Phe-Leu-Leu-Arg-Asn (SFLLRN) amino acids 1 to 6 of SEQ ID NO:1 and (iso-Ser)-Phe-Leu-Leu-Arg-Asn ((iso-S))FLLRN SEQ ID NO:7 studies, 2 mM peptide in buffer (0.15 M NaCl, 0.01 M Tris/HCl, pH 7.4) was mixed with an equal volume of citrated platelet-poor plasma (1:1) and separately with an equal volume of buffer and incubated at 37° C for variable periods of time. Aliquots were removed at 15, 30, 45, 60 and 120 minutes and analyzed for both the ability to aggregate platelets and peptide cleavage. Platelet aggregation was determined according the method described in Example 2 using a dual channel aggregometer except that final concentration of 2.2 µM for SFLLRN amino acids 1 to 6 of SEQ ID NO:1 and 8.8 µM for (iso-S)FLLRN SEQ ID NO:7 were chosen to give nearly comparable full scale deflections. The results are shown in FIG. 2.

Figure 3A:
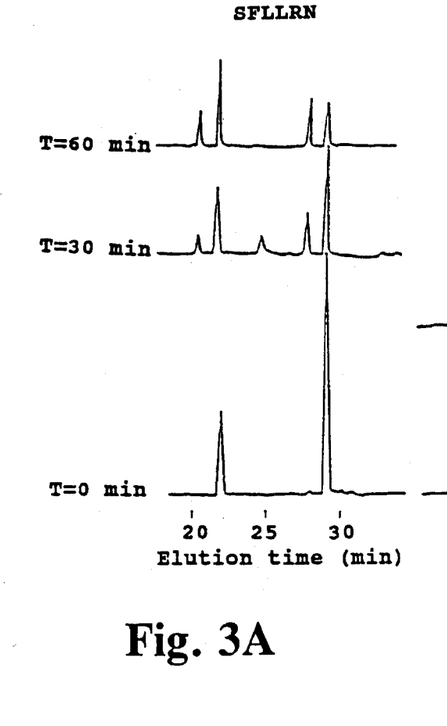
FIGS. 3A and B are comparisons of HPLC elution times of SFLLRN amino acids 1 to 6 of SEQ ID NO:1 and (iso-S)FLLRN SEQ ID NO:7 during plasma incubation.
Figure 3B:
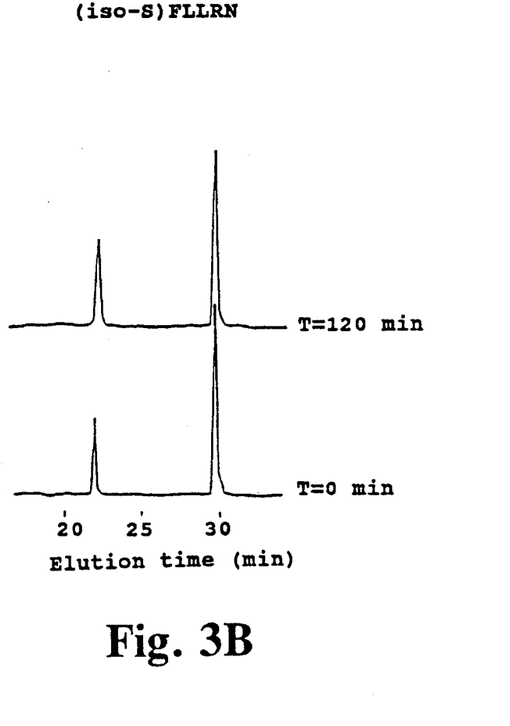

For peptide digestion studies for SFLLRN amino acids 1 to 6 of SEQ ID NO:1 and (iso-S)FLLRN SEQ ID NO:7, samples were removed at various times and analyzed for peptide digestion by HPLC after precipitating the plasma proteins with trichloroacetic acid. The results are shown in FIG. 3.

Time Course of Loss Of Peptide Aggregating Activity During Plasma Incubation The SFLLRN amino acids 1 to 6 of SEQ ID NO:1 peptide rapidly lost platelet aggregating activity when incubated in plasma whereas the (iso-S)FLLRN SEQ ID NO:7 peptide lost little if any activity even after 2 hours. These results are shown in FIG. 2. Decrease in optical density in FIG. 2B shows that the platelets have aggregated.

Thus, the (iso-S)FLLRN peptide retains its platelet aggregating activity to a much greater extent than does SFLLRN amino acids 1 to 6 of SEQ ID NO:1 when incubated with plasma. Similarly, the (DS)T-11 SEQ ID NO:11 retained more than half its aggregating activity when incubated with plasma for 1 hour, whereas T-11 amino acids 1 to 11 of SEQ ID NO:1 lost all of its aggregating activity within 1 hour (data not shown).

When either SFLLRN amino acids 1 to 6 of SEQ ID NO:1 or (iso-S)FLLRN SEQ ID NO:7 was incubated with buffer rather than plasma, there was no decrease in peptide activity after 2 hours (data not shown). Lower concentrations of the peptides (125 μM) were incubated with plasma. The SFLLRN amino acids 1 to 6 of SEQ ID NO:1 peptide lost all of its aggregating activity within 18 min. The (iso-S)FLLRN SEQ ID NO:7 peptide retained its full aggregating activity after 45 min. of incubation, but there was some decrease in activity after 1 hour; even at 2 hours, however, some aggregating activity remained.

Time Course of Peptide Digestion During Plasma Incubation

The HPLC elution time results of the plasma digestion in FIG. 3 show that when SFLLRN amino acids 1 to 6 of SEQ ID NO:1 (1 mM final concentration) was incubated with 50% platelet-poor plasma at 37° C., the SFLLRN peptide eluted at about 29 min. and the -(iso-S)-FLLRN SEQ ID NO:7 peptide eluted at about 30 min. The peak eluting at about 22 min. is derived from plasma and serves as an internal control. SFLLRN amino acids 1 to 6 of SEQ ID NO:1 underwent detectable cleavage within 10 min., progressing to nearly complete digestion by 2 hours. In contrast (iso-S)FLLRN SEQ ID NO:7 underwent minimal digestion even after 2 hours of precipitation. More specifically, with SFLLRN, amino acids 1 to 6 of SEQ ID NO:1 35% of the peptide was no longer intact after just 15 min. Digestion progressed rapidly with time, such that the percentage remaining intact decreased to 49%, 23%, 16% and 4% at 30, 45, 60 and 120 min. Virtually all of the (iso-S)FLLRN SEQ ID NO:7 peptide remained intact for the first 60 min., and even after 120 min. of incubation, ~83% of the peptide remained intact (FIG. 3).

---

We claim:

1. A polypeptide comprising formula I:

$R_1$-$R_2$-$R_3$-$R_4$-$R_5$-Z SEQ ID No:2 formula I wherein:

$R_1$ is isoserine 2,3-diaminopropanoate or 2,3 -dihydroxypropunoute $R_2$ is phenylalanine, p-fluorophenylalanine, p-methylphenylalanine or tryptophan $R_3$ leucine or phenylalanine $R_4$ is leucine $R_5$ arginine Z is carboxyl, carboxamide, one or more amino acids of amino acids 6 to 14 of SEQ ID No:1 or a moiety which enhances cell penetrating ability of the polypspride, said cell penetrating moiety selected from the group consisting of lipids, steroids, long chain amines and sugars; and wherein said polypeptide activates platelet aggregation and resists degradation by aminopeptidase M.

2. A method for resisting the inactivation of thrombin receptor peptide while activating platelet aggregation comprises administering an amount effective to induce platelet aggregation in the presence of aminopeptidase M, of a polypeptide comprising formula I $R_1$-$R_2$-$R_3$-$R_4$-$R_5$-Z SEQ ID No:2 formula I wherein:

$R_1$ is isoserine, 2,3-diaminopropanoate, or 2,3 -dihydroxypropanoate $R_2$ is phenylalanine, p-fluorophenylalanine, p-methylphenylalanine or tryptohan $R_3$ is leucine or pnenylalanine $R_4$ is leucine $R_5$ is arginine Z is carboxyl, carboxamide, one more amino acids of amino acids 6 to 14 of SEQ ID No:1 or a moiety which enhances cell penetrating ability of the polypeptide, said cell penetrating moiety selected from the group consisting of lipids, steroids, long chain amines and sugars.

3. A polypeptide which has the sequence (iso-Ser)-Phe-Leu-Leu-Arg-Asn-$NH_2$ SEQ ID NO:7.

4. A method for resisting the inactivation of thrombin receptor peptide while activating platelet aggregation comprises administering an amount effective to induce platelet aggregation in the presence of aminopeptidase M, of a polypeptide which has the sequence (iso-Ser)-Phe-Leu-Leu-Arg-Asn-$NH_2$ SEQ ID No:7.

* * * * *

UNITED STATES PATENT AND TRADEMARK OFFICE
CERTIFICATE OF CORRECTION

PATENT NO. : 5,455,228
DATED : October 3, 1995
INVENTOR(S) : Barry S. Coller, Glenn D. Prestwich Page 1 of 2

It is certified that error appears in the above-indentified patent and that said Letters Patent is hereby corrected as shown below:

On title page item [73],

|  | READS | SHOULD READ |
|---|---|---|
| The Assignee's city, | New York, New York | Albany, New York |
| Column 5, Lines 45-51 | | L-SFLLRN amino acids 1-6 (active) of SEQ ID NO:1 |

UNITED STATES PATENT AND TRADEMARK OFFICE
CERTIFICATE OF CORRECTION

PATENT NO. : 5,455,228
DATED : October 3, 1995
INVENTOR(S) : Barry S. Coller, Glenn D. Prestwich It is certified that error appears in the above-indentified patent and that said Letters Patent is hereby corrected as shown below:

| | | |
|---|---|---|
| Column 19, Lines 47-48, | 2,3-dihydroxypropunoute | 2,3-dihydroxypropanoate |
| Column 19, Line 56, | polyspride | polypeptide |
| Column 20, Line 47, | tryptohan | tryptophan |
| Column 20, Line 48, | pnenylalanine | phenylalanine |

Signed and Sealed this

Twenty-eighth Day of May, 1996

Attest:

BRUCE LEHMAN

Attesting Officer

Commissioner of Patents and Trademarks